United States Patent [19]

Gourbault

[11] Patent Number: 4,507,231

[45] Date of Patent: Mar. 26, 1985

[54] PROCESS FOR THE PREPARATION OF α-ASPARTYL PHENYLALANINE METHYL ESTER

[75] Inventor: Maurice J. Gourbault, Paris, France

[73] Assignee: Laboratoires Fournier S.A., Dijon, France

[21] Appl. No.: 522,165

[22] PCT Filed: Nov. 5, 1982

[86] PCT No.: PCT/FR82/00181
  § 371 Date: Jul. 5, 1983
  § 102(e) Date: Jul. 5, 1983

[87] PCT Pub. No.: WO83/01619
  PCT Pub. Date: May 11, 1983

[30] Foreign Application Priority Data

Nov. 5, 1982 [FR] France .................. 82 00181

[51] Int. Cl.$^3$ .................................................. C07C 103/52
[52] U.S. Cl. ......................................................... 260/112.5 R
[58] Field of Search ............................................. 260/112.5 R

[56] References Cited

U.S. PATENT DOCUMENTS

| | | | |
|---|---|---|---|
| 3,833,554 | 9/1974 | Ariyoshi et al. | 260/112.5 R |
| 3,879,372 | 4/1975 | Boesten | 260/112.5 R |
| 4,017,472 | 4/1977 | Farkas et al. | 260/112.5 R |
| 4,309,341 | 1/1982 | Kubo et al. | 260/112.5 R |

OTHER PUBLICATIONS

*Chemical Abstracts*, 86, 505 (1977); Abs. No. 155982w.
Battersby et al., *J. of the Chem. Soc.*, 259–269 (1955).

Primary Examiner—Delbert R. Phillips
Assistant Examiner—F. T. Moezie
Attorney, Agent, or Firm—Schwartz, Jeffery, Schwaab, Mack, Blumenthal & Koch

[57] ABSTRACT

The present invention relates to a process for the preparation of α-aspartyl phenylalanine methyl ester by reacting phenylalanine methyl ester with the anhydride of N-formyl L-aspartic acid, process wherein the product from said reaction is treated in at least one ion-exchanging resin column and the β-isomer contained in the resulting mixture is isomerized by treatment with acetic anhydride followed by an acid hydrolysis to convert said β-isomer into α-isomer and ensure the deformylation of said product.

5 Claims, No Drawings

PROCESS FOR THE PREPARATION OF α-ASPARTYL PHENYLALANINE METHYL ESTER

BACKGROUND OF THE INVENTION

The present invention relates to a process for the preparation of α-aspartyl phenylalanine methyl ester.

α-aspartyl phenylalanine methyl ester (or aspartam) is in great demand as an anti-caloric artificial sweetening agent. Its pharmacological and toxicological properties are now well known and its use does not involve any of the risks ascribed to the use of products such as saccharine and cyclohexylsulfamate.

It is also known that said aspartam should be used in its isomer form, because its β-isomer has no sweetening power and is on the contrary bitter in flavor.

It is therefore desirable to find a simple process for the synthesis of said aspartam, such process permitting to minimize the production of undesirable by-products (such as said β-isomer) and comprising a valorizing technique by conversion of said β-isomer into an α-isomer.

SUMMARY OF THE INVENTION

The process comprises condensing in known manner in an aqueous base medium, phenylalaline methyl ester with the anhydride of N-formyl L-aspartic acid and then treating the product from said condensation reaction in at least one ion-exchanging resin column, in which acidification of said product takes place and after recovery of the N-formyl isomer, on the one hand, and of a mixture of N-formyl α- and β-isomers, on the other hand, treating the mixture of α- and β-isomers with acetic anhydride in order to obtain the corresponding aspartimide. The resulting product is then treated with an acid so as to convert into α-isomer the largest part of the β-isomer contained in said mixture and to ensure deformylation of said products.

DETAILED DESCRIPTION OF PREFERRED EMBODIMENTS

As already indicated, the condensation reaction of phenylalanine methyl ester with anhydride of N-formyl L-aspartic acid is known. It is known, on the one hand, because it is but a novel use of the general condensation process of two aminoacids, and on the other hand, because it has been described in a number of documents, including French Pat. Nos. 2 040 473, 2 078 640 and 2 160 471.

But the techniques wherein, at the end of the condensation reaction described hereinabove, the products which have formed are recovered with a view to preparing the pure α-isomer of aspartam, are of major importance in making said process commercially viable and in giving a final product which is as pure as possible.

In the present invention, the reaction product is therefore subjected to an acidification by being directed through an ion-exchanging column containing a resin of the sulfonic polystyrene type. This results, on the one hand, in the conversion of the sodium salts formed during the condensation reaction into corresponding acids, and on the other hand, in the demineralization of the medium. There is thus obtained a product (aspartam comprising a formyl blockage) containing more than about 80% of α-isomer of N-formyl aspartam; the α-isomer content of the eluate is such that it is possible, after concentration, to precipitate a solid crystalline product by simple seeding of the concentrated eluate with crystals of N-formyl aspartam α-isomer.

The advantage of such a treatment is obvious.

The N-formyl aspartam of α-form thus obtained can be deformylated by known techniques, such as by treatment with hydrochloric acid diluted at temperatures of between 30° and 75° C., in order to obtain aspartam.

But, on the other hand, the condensation process produces N-formyl aspartam of β-form which is recovered as such or which is mostly in the form of mixtures with N-formyl aspartam of α-form. It is therefore desirable to have a process permitting to convert said β-isomer into α-isomer.

According to the present invention, isomerization of the β-isomer into α-isomer and deformylation of the starting mixture are simultaneously carried out by the conversion described hereinafter.

Said conversion comprises:
in a first stage, reacting the β-isomer or a mixture of the aspartam α- and β-isomers with acetic anhydride; this reaction takes place at between 10° and 70° C. in solution in the anhydride and leads to the formation of an aspartimide of formula:

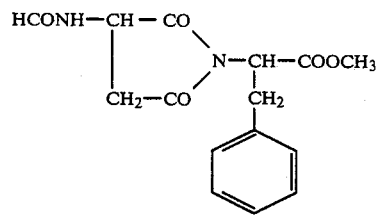

in a second stage, subjecting the aspartimide to a hydrolysis in solution and in an acid medium (pH between 2.5 and 3.5) to obtain the α-isomer of aspartam;
the solution obtained is crystallized to recover the pure product.

The following example is given non-restrictively to illustrate the various aspects of the invention.

EXAMPLE 1

Treatment of the condensation product of phenylalanine methyl ester with anhydride of N-formyl aspartic acid.

The condensation reaction was carried out using substantially equivalent quantities, by weight, of the two reagents and an aqueous soda solution. The pH was adjusted to 8.5 and the temperature to 0° C. The reaction lasting about 2 hours.

The resulting cold solution was percolated on a duolite 0-20 sulfonic resin colum; the volume of the column was proportional to the quantities to be treated and the elution rate was determined by solutions.

A very acid percolate was obtained wherein the pH was adjusted to about 2.4 by addition of sodium hydroxide; the precipitated calcium sulfate was filtered.

The filtrate was again percolated over the same column and in the same conditions, in particular, to remove the non-fixed sodium and the residual calcium.

The percolate was concentrated under vacuum.

A solution was obtained which crystallizes by simple addition of N-formyl α-aspartam crystals.

The crystals obtained contained at least 80% of the α-isomer of N-formyl aspartam and could be purified by recrystallization.

EXAMPLE 2

Isomerization and deformylation of the mixture of α- and β-isomers of N-formyl aspartam.

By carrying out the same condensation reaction as described in Example 1, there was also obtained a solution containing, in substantially similar proportions, the α-isomer of N-formyl aspartam and the β-isomer of the same product.

This solution was then treated as follows:

about 2 kg of this precipitate and 10 kg of acetic anhydride were placed in a reactor; the mixture was brought to 60° C. for one hour; then it was concentrated under vacuum until a precipitate or an oil was obtained.

the resulting precipitate (or oil) was dissolved in methanol and an adequate quantity of hydrochloric acid was added so that the pH of the medium was between about 2.5 and 3.5; the mixture was heated for one hour at 60° C.

the α-isomer of aspartam was directly obtained by crystallisation. In these reactions, isomerisation of the β-isomer of N-formyl aspartam and deformylation of said isomer were carried out simultaneously.

I claim:

1. A process for producing N-formyl α-aspartam, comprising the steps of:
    (1) preparing a mixture comprised of α-isomer and β-isomer of N-formyl aspartam;
    (2) heating said mixture in the presence of acetic anhydride to a temperature between about 10° and about 70° C., such that said N-formyl aspartam is converted to the corresponding aspartimide; and thereafter
    (3) hydrolyzing said aspartimide in an acid solution at a pH in the range between about 2.3 and about 3.5, such that said β-isomer is converted to α-isomer.

2. A process according to claim 1, wherein step (1) comprises the condensation of phenylalanine methyl ester with N-formyl aspartic acid anhydride.

3. A process according to claim 2, wherein step (1) further comprises acidifying the product of said condensation of said phenylalanine methyl ester by passing said product through an ion-exchanging resin column.

4. A process according to claim 3, wherein said ion-exchanging resin column comprises a sulfonic polystyrene resin.

5. A process according to claim 1, wherein step (3) comprises dissolving said aspartimide in methanol and adding hydrochloric acid thereto.

* * * * *

UNITED STATES PATENT AND TRADEMARK OFFICE
CERTIFICATE OF CORRECTION

PATENT NO. : 4,507,231

DATED : March 26, 1985

INVENTOR(S) : Maurice Jean GOURBAULT

It is certified that error appears in the above—identified patent and that said Letters Patent is hereby corrected as shown below:

On the title page;

--[30] Foreign Application Priority Data

Nov. 6, 1981 [FR] France ..................81 20877--

Signed and Sealed this

Thirteenth Day of August 1985

[SEAL]

Attest:

DONALD J. QUIGG

Attesting Officer

Acting Commissioner of Patents and Trademarks